US011266322B2

(12) United States Patent
Ito

(10) Patent No.: US 11,266,322 B2
(45) Date of Patent: Mar. 8, 2022

(54) BLOOD FLOW ANALYSIS APPARATUS, BLOOD FLOW ANALYSIS METHOD, AND BLOOD FLOW ANALYSIS PROGRAM

(71) Applicant: FUJIFILM Corporation, Tokyo (JP)

(72) Inventor: Hirotaka Ito, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 296 days.

(21) Appl. No.: 16/546,876

(22) Filed: Aug. 21, 2019

(65) Prior Publication Data
US 2019/0374114 A1  Dec. 12, 2019

Related U.S. Application Data

(63) Continuation of application No. PCT/JP2018/007610, filed on Feb. 28, 2018.

(30) Foreign Application Priority Data

Feb. 28, 2017  (JP) .............................. JP2017-037060

(51) Int. Cl.
*A61B 5/0285* (2006.01)
*G16H 50/50* (2018.01)
(Continued)

(52) U.S. Cl.
CPC ............ *A61B 5/0285* (2013.01); *A61B 5/055* (2013.01); *A61B 5/7425* (2013.01); *A61B 8/06* (2013.01); *A61B 8/483* (2013.01); *G16H 50/50* (2018.01)

(58) Field of Classification Search
CPC ..... A61B 5/0285; A61B 5/055; A61B 5/7425; A61B 8/06; A61B 8/483; A61B 8/5223;
(Continued)

(56) References Cited

U.S. PATENT DOCUMENTS

2004/0019264 A1  1/2004  Suurmond et al.
2015/0370995 A1  12/2015  Wakai

FOREIGN PATENT DOCUMENTS

JP  H08-150142 A  6/1996
JP  2004-201730 A  7/2004
(Continued)

OTHER PUBLICATIONS

Li et al., Quantification of chronic aortic regurgitation by vector flow mapping: a novel echocardiographic method, European Journal of Echocardiography (2010) 11, 119-124.*
(Continued)

*Primary Examiner* — Bo Joseph Peng
(74) *Attorney, Agent, or Firm* — Studebaker & Brackett PC

(57) ABSTRACT

The blood flow analysis apparatus includes a blood vessel region extraction unit that extracts a blood vessel region from a blood vessel image obtained by capturing an image of an object including a blood vessel; a flow velocity vector acquisition unit that acquires a flow velocity vector indicating a blood flow velocity and a blood flow direction in the blood vessel region; and a back flow specification unit that sets a central axis which extends in an extension direction of the blood vessel region, integrates a component of the flow velocity vector in a direction of the central axis with respect to a time axis to calculate an integral value, and specifies whether there is a blood back flow in the blood vessel region on the basis of a change in the integral value.

15 Claims, 4 Drawing Sheets

(51) Int. Cl.
    *A61B 5/055*     (2006.01)
    *A61B 5/00*     (2006.01)
    *A61B 8/06*     (2006.01)
    *A61B 8/08*     (2006.01)

(58) Field of Classification Search
    CPC ......... A61B 8/466; A61B 8/488; A61B 6/032; A61B 6/504; A61B 6/507; A61B 8/0891; A61B 5/0263; G16H 50/50; G16H 30/40; G16H 50/30
    See application file for complete search history.

(56) References Cited

FOREIGN PATENT DOCUMENTS

| | | |
|---|---|---|
| JP | 2005-533593 A | 11/2005 |
| JP | 2009-153919 A | 7/2009 |
| JP | 2010-075636 A | 4/2010 |
| JP | 2014-188323 A | 10/2014 |

OTHER PUBLICATIONS

Thavendiranathan et al., Quantification of Chronic Functional Mitral Regurgitation by Automated 3-Dimensional Peak and Integrated Proximal Isovelocity Surface Area and Stroke Volume Techniques Using Real-Time 3-Dimensional Volume Color Doppler Echocardiography In Vitro and Clinical Validation, Circ Cardiovasc Imag.*

Garcia et al., Estimating cardiac output. Utility in the clinical practice. Available invasive and non-invasive monitoring, Medicina Intensiva (English Edition), vol. 35, Issue 9, 2011, pp. 552-561, ISSN 2173-5727.*

Miyamoto et al., Quantification of Mitral Regurgitation by Proximal Isovelocity Surface Area Method in Patients with Mitral Valve Prolapse: The Japan Society of Ultrasonics in Medicine, Oct. 15, 1993, vol. 20, Supplement II, pp. 203-204.

Wugang Wang et al., Quantification of Mitral Regurgitation by General Imaging Three-Dimensional Quantification: Feasibility and Accuracy, J Am Soc Echocardiogr. (American Society of Echocardiography), Mar. 2014, vol. 27, Issue 3, pp. 268-276.

International Search Report issued in PCT/JP2018/007610; dated May 1, 2018.

Written Opinion issued in PCT/JP2018/007610; dated May 1, 2018.

\* cited by examiner

BLOOD FLOW ANALYSIS APPARATUS, BLOOD FLOW ANALYSIS METHOD, AND BLOOD FLOW ANALYSIS PROGRAM

CROSS-REFERENCE TO RELATED APPLICATION

This application is a continuation application of International Application No. PCT/JP2018/007610, filed Feb. 28, 2018, the disclosure of which is incorporated herein by reference in its entirety. Further, this application claims priority from Japanese Patent Application No. 2017-037060, filed Feb. 28, 2017 the disclosure of which is incorporated herein by reference in its entirety.

BACKGROUND OF THE INVENTION

Field of the Invention

The present invention relates to a blood flow analysis apparatus, a blood flow analysis method, and a blood flow analysis program that analyze a blood flow in a blood vessel region extracted from a medical image, using the blood vessel region.

Related Art

In recent years, for example, a method has been used which analyzes a blood flow in a blood vessel of the heart using a medical image of the heart.

As the blood flow analysis method using the medical image, for example, a method has been proposed which calculates a flow velocity vector for each voxel, each pixel, or each region, using a magnetic resonance imaging (MRI) image captured by a three-dimensional cine phase contrast magnetic resonance method and displays the flow velocity vector.

In addition, JP2014-188323A discloses a technique which generates a blood vessel model from a medical image and calculates a flow velocity vector on the basis of the blood vessel model, using computational fluid dynamics (CFD).

Here, in blood flow analysis, it is important to specify a portion in which a blood back flow occurs in terms of diagnosis. In a case in which the flow velocity vector is displayed as described above, the user observes the direction and magnitude of the flow velocity vector to specify the back flow portion.

In addition, a region of interest is set in a blood vessel region extracted from a medical image and a flow line indicating a blood flow in the region of interest is displayed so as to be observed, which makes it possible to check a back flow.

Further, a back flow is checked in the field of ultrasonic diagnosis. For example, JP2009-153919A and JP1996-150142A (JP-H08-150142A) disclose a technique which performs color Doppler measurement with an ultrasound diagnostic apparatus to visualize a back flow.

However, in a case in which the three-dimensional cine phase contrast magnetic resonance method and the CFD are used to check the back flow portion, the user can check the back flow portion by checking the direction of the flow velocity vector in the vicinity of a portion of interest or by checking the formation of the flow line in a case in which the region of interest is set. In this case, if there is a back flow in portions other than the portion observed by the user for a certain purpose, the user is likely to overlook the back flow.

In addition, in a case in which a back flow is checked by ultrasound diagnosis, the user brings a probe into contact with the region of interest and color Doppler measurement is performed. An ultrasound image is a two-dimensional image and it is possible to display forward and backward flows on the two-dimensional image. However, it is difficult to extract a flow along the shape of the blood vessel and to visualize a back flow.

SUMMARY

The invention has been made in view of the above-mentioned problems and an object of the invention is to provide a blood flow analysis apparatus, a blood flow analysis method, and a blood flow analysis program that can recognize a back flow portion even in a case in which a back flow occurs in an unexpected portion and reduce the risk of overlooking the back flow portion.

According to the invention, there is provided a blood flow analysis apparatus comprising: a blood vessel region extraction unit that extracts a blood vessel region from a blood vessel image obtained by capturing an image of an object including a blood vessel; a flow velocity vector acquisition unit that acquires a flow velocity vector indicating a blood flow velocity and a blood flow direction in the blood vessel region; and a back flow specification unit that sets a central axis which extends in an extension direction of the blood vessel region, integrates a component of the flow velocity vector in a direction of the central axis with respect to a time axis to calculate an integral value, and specifies whether there is a blood back flow in the blood vessel region on the basis of a change in the integral value.

In the blood flow analysis apparatus according to the invention, the back flow specification unit may specify that there is the back flow in a case in which the integral value does not increase or decrease monotonically.

The blood flow analysis apparatus according to the invention may further comprise a display control unit that displays a map image obtained by mapping a portion in which the back flow occurs to a coordinate axis of the blood vessel region on a display unit.

In the blood flow analysis apparatus according to the invention, the display control unit may generate the map image using the integral value obtained by integrating the flow velocity vector for a predetermined period.

In the blood flow analysis apparatus according to the invention, the predetermined period may be a period of one heartbeat.

In the blood flow analysis apparatus according to the invention, the display control unit may generate the map image in time series whenever the flow velocity vector is integrated in the direction of the time axis and display the map image as a moving image on the display unit.

In the blood flow analysis apparatus according to the invention, the display control unit may display the map image so as to be superimposed on a two-dimensional or three-dimensional blood vessel image.

In the blood flow analysis apparatus according to the invention, the display control unit may display information of an amount of the back flow on the display unit on the basis of the integral value.

In the blood flow analysis apparatus according to the invention, the display control unit may display an index indicating a blood flow other than the map image on the display unit.

In the blood flow analysis apparatus according to the invention, the index indicating the blood flow may be the flow velocity vector, a flow line, or a path line.

In the blood flow analysis apparatus according to the invention, the back flow specification unit may calculate the integral value for each voxel or each group of a plurality of voxels in the blood vessel region.

In the blood flow analysis apparatus according to the invention, the back flow specification unit may calculate the integral value for each cross section that is orthogonal to a direction of the central axis of the blood vessel region.

In the blood flow analysis apparatus according to the invention, the flow velocity vector acquisition unit may acquire the flow velocity vector on the basis of a three-dimensional blood vessel image captured in time series or a three-dimensional blood vessel image captured at any point of time.

In the blood flow analysis apparatus according to the invention, the flow velocity vector acquisition unit may acquire the flow velocity vector, using a computational fluid dynamics model for the blood vessel region, a three-dimensional cine phase contrast magnetic resonance method, or a three-dimensional ultrasound image.

According to the invention, there is provided a blood flow analysis method comprising: extracting a blood vessel region from a blood vessel image obtained by capturing an image of an object including a blood vessel; acquiring a flow velocity vector indicating a blood flow velocity and a blood flow direction in the blood vessel region; and setting a central axis which extends in an extension direction of the blood vessel region, integrating a component of the flow velocity vector in a direction of the central axis with respect to a time axis to calculate an integral value, and specifying whether there is a blood back flow in the blood vessel region on the basis of a change in the integral value.

According to the invention, there is provided a blood flow analysis program that causes a computer to function as: a blood vessel region extraction unit that extracts a blood vessel region from a blood vessel image obtained by capturing an image of an object including a blood vessel; a flow velocity vector acquisition unit that acquires a flow velocity vector indicating a blood flow velocity and a blood flow direction in the blood vessel region; and a back flow specification unit that sets a central axis which extends in an extension direction of the blood vessel region, integrates a component of the flow velocity vector in a direction of the central axis with respect to a time axis to calculate an integral value, and specifies whether there is a blood back flow in the blood vessel region on the basis of a change in the integral value.

Another blood flow analysis apparatus according to the invention comprises a memory that stores commands to be executed by a computer and a processor that is configured to execute the stored commands. The processor performs a process of extracting a blood vessel region from a blood vessel image obtained by capturing an image of an object including a blood vessel; a process of acquiring a flow velocity vector indicating a blood flow velocity and a blood flow direction in the blood vessel region; and a process of setting a central axis which extends in an extension direction of the blood vessel region, integrating a component of the flow velocity vector in a direction of the central axis with respect to a time axis to calculate an integral value, and specifying whether there is a blood back flow in the blood vessel region on the basis of a change in the integral value.

According to the blood flow analysis apparatus, the blood flow analysis method, and the blood flow analysis program of the invention, a blood vessel region is extracted from a blood vessel image obtained by capturing an image of an object including a blood vessel and a flow velocity vector indicating a blood flow velocity and a blood flow direction in the blood vessel region is acquired. Then, a central axis which extends in an extension direction of the blood vessel region is set and a component of the flow velocity vector in a direction of the central axis is integrated in a direction of a time axis to calculate an integral value. Then, it is specified whether there is a blood back flow in the blood vessel region on the basis of a change in the integral value. As such, it is specified whether there is a back flow on the basis of the integral value of the component of the flow velocity vector in the direction of the central axis. Therefore, even in a case in which a back flow occurs in an unexpected portion, it is possible to recognize the back flow portion and to reduce the risk of overlooking the back flow portion.

DETAILED DESCRIPTION

Figure 1:
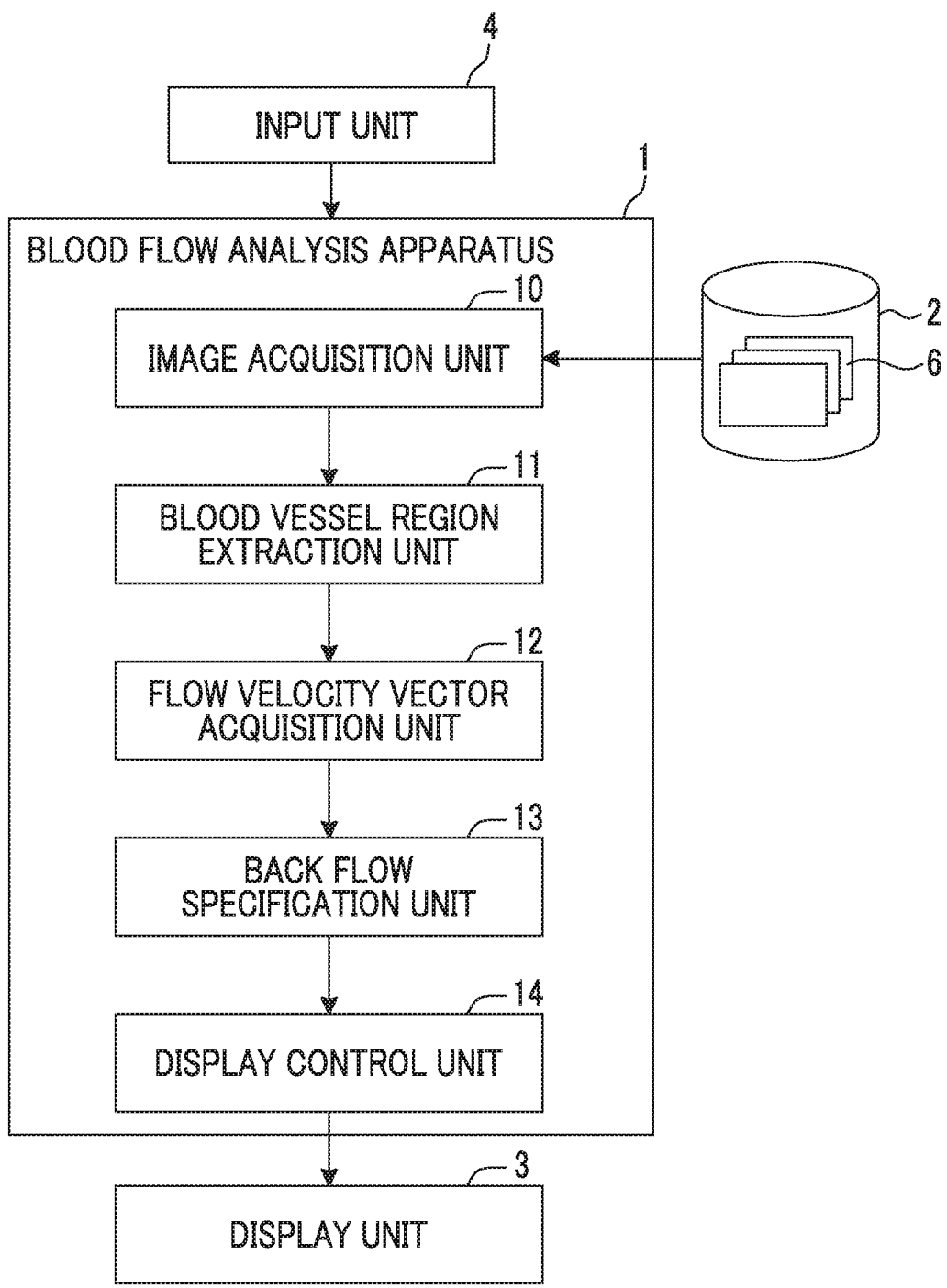
FIG. 1 is a block diagram schematically illustrating the configuration of a blood flow analysis system using an embodiment of a blood flow analysis apparatus according to the invention.

Hereinafter, a blood flow analysis system using an embodiment of a blood flow analysis apparatus according to the invention will be described with reference to the drawings. FIG. 1 is a block diagram schematically illustrating the configuration of the blood flow analysis system according to this embodiment.

Specifically, as illustrated in FIG. 1, the blood flow analysis system according to this embodiment comprises a blood flow analysis apparatus 1, a medical image storage server 2, a display unit 3, and an input unit 4.

The blood flow analysis apparatus 1 is configured by installing a blood flow analysis program according to this embodiment in a computer.

The blood flow analysis apparatus 1 comprises a central processing unit (CPU), a semiconductor memory, and a storage device such as a hard disk drive or a solid state drive (SSD). The blood flow analysis program according to this embodiment is installed in the storage device and the central processing unit executes the blood flow analysis program such that an image acquisition unit 10, a blood vessel region extraction unit 11, a flow velocity vector acquisition unit 12, a back flow specification unit 13, and a display control unit 14 illustrated in FIG. 1 operate.

The blood flow analysis program is recorded on a recording medium, such as a digital versatile disc (DVD) or a compact disc read only memory (CD-ROM), is distributed, and is then installed in the computer from the recording medium. Alternatively, the blood flow analysis program is stored in a storage device of a server computer connected to the network or a network storage so as to be accessed from the outside. Then, the blood flow analysis program is downloaded to the computer in response to a request from the outside and is then installed in the computer.

The image acquisition unit 10 acquires a medical image of a patient that has been captured in advance. In this embodiment, the image acquisition unit 10 acquires three-dimensional medical images 6 captured by, for example, a computed tomography (CT) apparatus, a magnetic resonance imaging (MRI) apparatus, and an ultrasound imaging apparatus. In this embodiment, a case in which the three-dimensional medical image 6 (corresponding to a blood vessel image according to the invention) of the heart of the patient (corresponding to an object according to the invention) is acquired will be described. However, the invention is not limited thereto. The object may be other organs such as the lungs, the liver, and the head.

The three-dimensional medical image 6 is stored in advance in the medical image storage server 2 together with the identification information of the patient. The image acquisition unit 10 reads a three-dimensional medical image 6 having the identification information of the patient input by the user through, for example, the input unit 4 from the medical image storage server 2 on the basis of the identification information and temporarily stores the three-dimensional medical image 6.

The blood vessel region extraction unit 11 extracts a blood vessel region from the three-dimensional medical image 6. Specifically, the blood vessel region extraction unit 11 according to this embodiment extracts a coronary region as the blood vessel region from the three-dimensional medical image 6 of the heart. For example, the blood vessel region extraction unit 11 performs multi-resolution conversion for the three-dimensional medical image 6 of the heart, performs Hessian matrix eigenvalue analysis for images with each resolution, and integrates the analysis results of the images with each resolution to extract the coronary region as an aggregate of linear structures (vessels) with various sizes in the heart region (for example, see Y Sato, et al., "Three-dimensional multi-scale line filter for segmentation and visualization of curvilinear structures in medical images.", Medical Image Analysis, June 1998, Vol. 2, No. 2, pp. 143-168). In addition, the coronary region may be extracted as follows: the center points of the extracted line structures are connected by, for example, a minimum spanning tree algorithm to generate tree structure data indicating the coronary artery; at each point (each node of the tree structure data) on a core line connecting the center points of the coronary arteries, a cross section orthogonal to the core line is calculated; in each cross section, the contour of the coronary artery is recognized by a known segmentation method such as a graph cut method; and information indicating the contour is associated with each node of the tree structure data.

In addition, a method for extracting the coronary region is not limited to the above-mentioned method and other known methods including a region expansion method may be used.

The flow velocity vector acquisition unit 12 acquires a flow velocity vector indicating a blood flow velocity and a blood flow direction in the blood vessel region. Various methods can be used to acquire the flow velocity vector. Specifically, for example, blood flow analysis is performed by computational fluid dynamics (CFD) using the blood vessel region extracted by the blood vessel region extraction unit 11 to acquire the flow velocity vector. At that time, blood flow analysis may be performed using the blood vessel region extracted from the three-dimensional medical image 6 captured at any point of time or blood flow analysis may be performed using the blood vessel region extracted from the three-dimensional medical image 6 captured in time series.

Further, the image acquisition unit 10 may acquire an MRI image captured by a three-dimensional cine phase contrast magnetic resonance method (3D cine PC MRI) and the flow velocity vector may be acquired using velocity information of the blood vessel region acquired on the basis of the MRI image.

Figure 2:
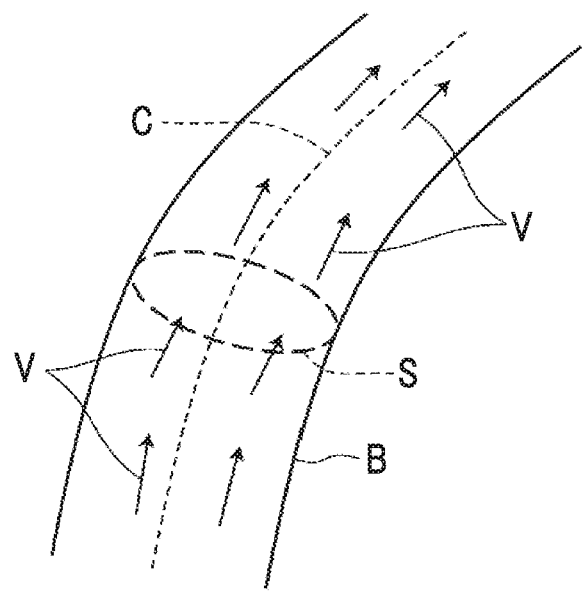
FIG. 2 is a diagram schematically illustrating a flow velocity vector in a blood vessel region.

In addition, the image acquisition unit 10 may acquire a three-dimensional ultrasound image captured in time series by Doppler measurement and the flow velocity vector may be acquired using velocity information of the blood vessel region acquired on the basis of the ultrasound image. FIG. 2 is a diagram schematically illustrating a flow velocity vector V in a blood vessel region B.

The back flow specification unit 13 specifies whether there is a blood back flow in the blood vessel region on the basis of the flow velocity vector in the blood vessel region acquired by the flow velocity vector acquisition unit 12.

Specifically, as illustrated in FIG. 2, the back flow specification unit 13 sets a central axis C that extends in the extension direction of the blood vessel region B, integrates a component of the flow velocity vector V in the direction of the central axis C with respect to the time axis to calculate an integral value, and specifies whether there is a blood back flow in the blood vessel region on the basis of a change in the integral value.

Figure 3:
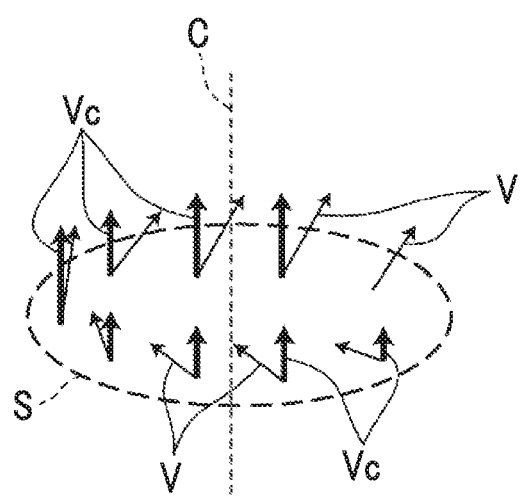
FIG. 3 is a diagram illustrating a method for specifying a back flow portion.
Figure 4:
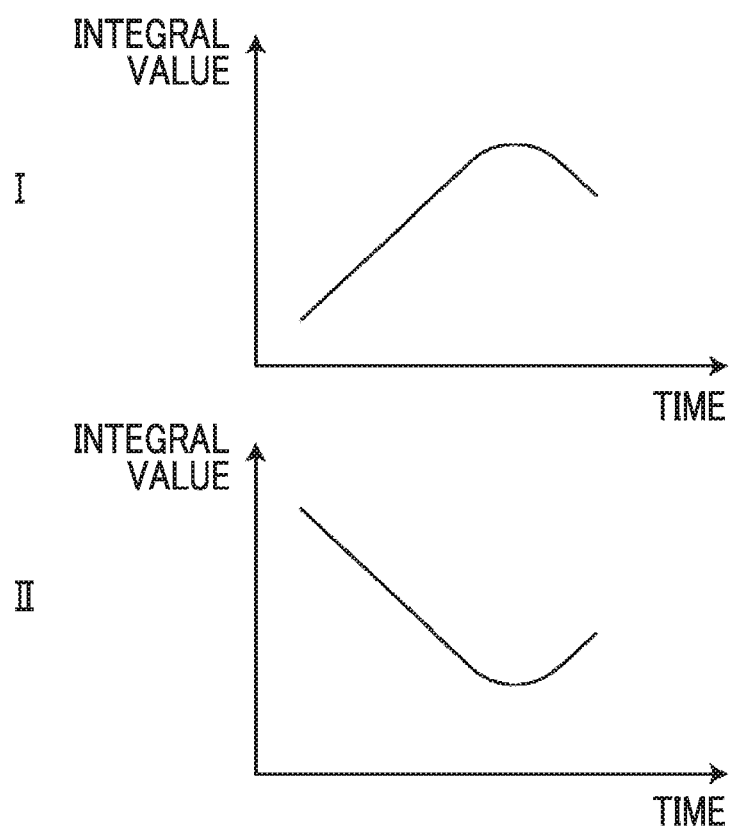
FIG. 4 is a diagram illustrating an example in which an integral value increases or decreases monotonically.

For the component of the flow velocity vector V in the direction of the central axis C, for example, as illustrated in FIGS. 2 and 3, a cross section S orthogonal to the central axis C is set for each point on the central axis C and a component Vc of the flow velocity vector V in the direction of the central axis in the cross section S is calculated. Then, the component Vc in the direction of the central axis is integrated in the direction of the time axis to calculate an integral value and it is determined whether the integral value increases or decreases monotonically. That is, for example, in a case in which there is no back flow in the blood vessel region, the integral value increases or decreases monotonically. On the other hand, in a case in which there is a back flow in the blood vessel region, the component Vc of the flow velocity vector V in the direction of the central axis is changed in a reverse direction. Therefore, the integral value of the component Vc in the direction of the central axis does not increase or decrease monotonically as illustrated in FIG. 4I or 4II.

Therefore, in a case in which the integral value of the component Vc in the direction of the central axis increases or decreases monotonically, the back flow specification unit 13 determines that there is no back flow. In a case in which the integral value of the component Vc in the direction of the central axis does not increase or decrease monotonically, the back flow specification unit 13 determines that there is a back flow. In addition, the mean or the median of the integral values of the components Vc in the direction of the central axes of each flow velocity vector V in the cross section S may be used as the integral value of the component Vc in the direction of the central axis.

Further, the user can set the interval between the cross sections S orthogonal to the central axis C of the blood vessel region B in the direction of the central axis to any interval. In addition, the user can set an integration period in a case in which the integral value is calculated to any interval. In a case in which it is specified whether there is a blood back flow in the blood vessel of the heart as in this embodiment, it is preferable that the integration period is a period of one heartbeat.

Figure 5:
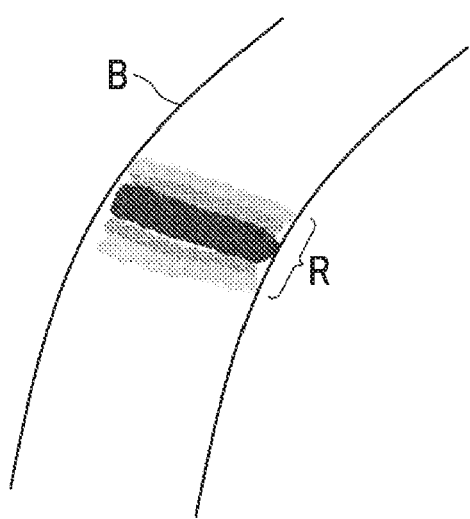
FIG. 5 is a diagram illustrating an example of the display of the back flow portion in a case in which the integral value is calculated for each cross section.

Returning to FIG. 1, the display control unit 14 displays information of a back flow portion specified by the back flow specification unit 13 on the display unit 3. Specifically, the display control unit 14 generates a map image obtained by mapping the back flow portion on the coordinate axis of the blood vessel region and displays the map image on the display unit 3. FIG. 5 is a diagram illustrating an example of the map image obtained by mapping a back flow portion R on the coordinate axis of the blood vessel region B. In this embodiment, as described above, a cross section orthogonal to the central axis of the blood vessel region is set and an integral value for each cross section is calculated. Therefore, as illustrated in FIG. 5, the back flow portion R is displayed for each cross section.

In addition, the integral value calculated for each cross section indicates the amount of back flow. Therefore, an image indicating the amount of back flow is displayed by changing display depending on the integral value. At that time, an image indicating the amount of back flow may be generated on the basis of the integral value for the entire integration period and then displayed. In this way, a still image may be displayed. Alternatively, an image indicating the amount of back flow may be sequentially generated whenever the flow velocity vector is integrated in the direction of the time axis, that is, for each integral value in each integration process within the integration period and then displayed. In this way, a moving image may be displayed.

The configuration in which the image indicating the amount of back flow is displayed makes it possible to intuitively recognize the amount of back flow and can be helpful in diagnosis and treatment.

The map image illustrated in FIG. 5 is an image of a map image in which, as the integral value becomes larger, density becomes higher. It is preferable that a color image is displayed as the map image. In this case, it is desirable to change a color or chroma depending on the integral value.

In addition, the map image may be displayed so as to be superimposed on the three-dimensional medical image 6. Further, the image on which the map image is superimposed is not limited to the three-dimensional medical image 6. For example, the map image may be displayed so as to be superimposed on a two-dimensional cross-sectional image.

Returning to FIG. 1, the medical image storage server 2 is a computer that stores and manages various types of data and comprises a high-capacity storage device and a database management program. The medical image storage server 2 acquires, for example, the three-dimensional medical image 6 captured in advance from an imaging apparatus, such as a CT apparatus or an MRI apparatus, through the network, stores the three-dimensional medical image 6 in the high-capacity storage device, and manages the three-dimensional medical image 6.

The input unit 4 receives the input of various settings by the user and comprises an input device such as a keyboard or a mouse. For example, the input unit 4 receives the input of the setting of the identification information of the patient.

Figure 6:
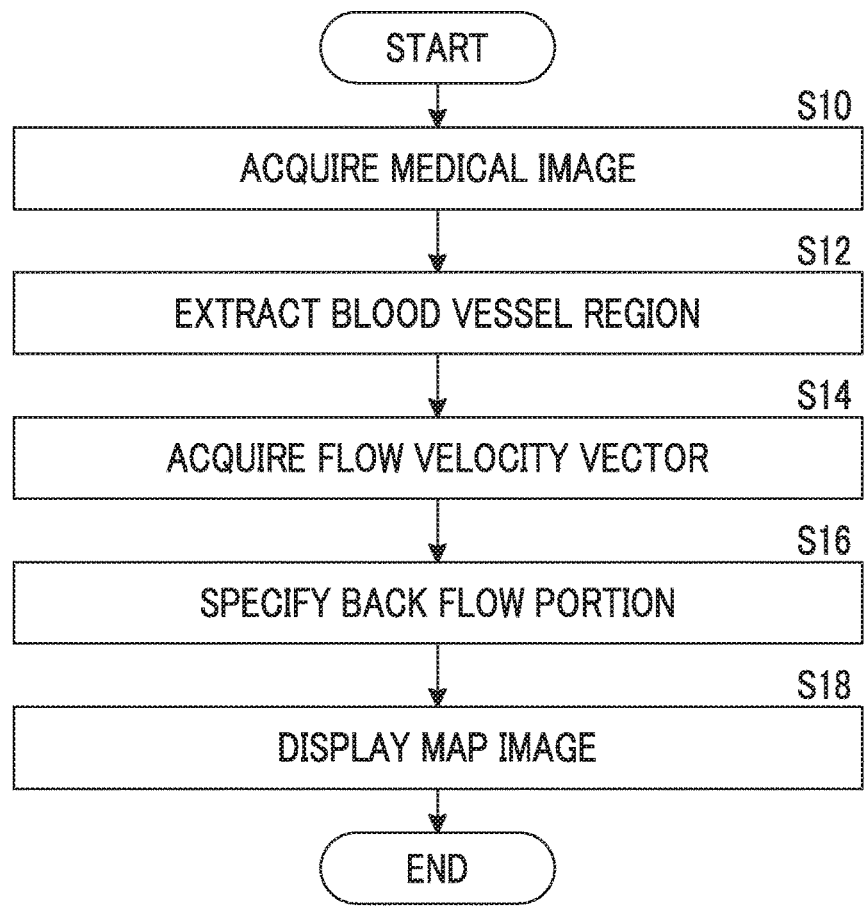
FIG. 6 is a flowchart illustrating the operation of the blood flow analysis system using an embodiment of the blood flow analysis apparatus according to the invention.

Next, the operation of the blood flow analysis system according to this embodiment will be described with reference to FIG. 6.

First, the image acquisition unit 10 acquires a medical image of a patient in response to, for example, the input of the setting of, for example, the identification information of the patient by the user (S10). In this embodiment, as described above, the three-dimensional medical image 6 of the heart is acquired.

Then, the three-dimensional medical image 6 of the heart acquired by the image acquisition unit 10 is input to the blood vessel region extraction unit 11 and the blood vessel region extraction unit 11 extracts a blood vessel region from the input three-dimensional medical image 6 (S12).

Then, the flow velocity vector acquisition unit 12 performs blood flow analysis with, for example, CFD using the blood vessel region to acquire a flow velocity vector in the blood vessel region (S14). Then, the back flow specification unit 13 specifies whether there is a blood back flow on the basis of the flow velocity vector in the blood vessel region. Specifically, as described above, the back flow specification unit 13 sets a central axis that extends in the extension direction of the blood vessel region, integrates the component of the flow velocity vector in the direction of the central axis with respect to the time axis to calculate an integral value, and specifies whether there is a blood back flow in the blood vessel region on the basis of a change in the integral value (S16).

Then, the information of the back flow portion specified by the back flow specification unit 13 is output to the display control unit 14 and the display control unit 14 generates a map image on the basis of the input information and displays the map image on the display unit 3 (S18).

According to the blood flow analysis system of the above-described embodiment, a blood vessel region is extracted from a blood vessel image obtained by capturing an image of an object including a blood vessel and a flow velocity vector indicating a blood flow velocity and a blood flow direction in the blood vessel region is acquired. Then, a central axis that extends in the extension direction of the blood vessel region is set and the component of the flow velocity vector in the direction of the central axis is integrated in the direction of the time axis to calculate an integral value. Then, it is specified whether there is a blood back flow in the blood vessel region on the basis of a change in the integral value. As such, it is specified whether there is a back flow on the basis of the integral value of the component of the flow velocity vector in the direction of the central axis. Therefore, even in a case in which a back flow occurs in an unexpected portion, it is possible to recognize the back flow portion and to reduce the risk of overlooking the back flow portion.

Figure 7:
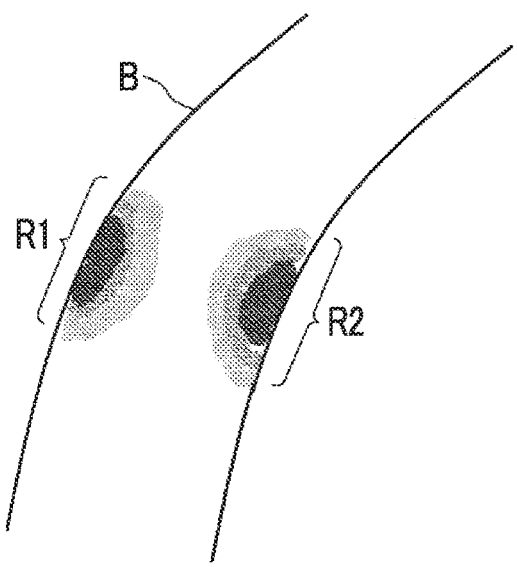
FIG. 7 is a diagram illustrating an example of the display of the back flow portion in a case in which the integral value is calculated for each group of a plurality of voxels.

In the blood flow analysis system according to the above-described embodiment, the integral value of the flow velocity vector is calculated for each cross section orthogonal to the direction of the central axis of the blood vessel region. However, the invention is not limited thereto. For example, the integral value may be calculated for each voxel or each group of a plurality of voxels in the blood vessel region. FIG. 7 is a diagram illustrating an example in which the integral value is calculated for each group of a plurality of voxels and back flow portions R1 and R2 are specified to generate a map image. For example, the mean or median of the integral values calculated for each of the plurality of voxels may be used as the integral value for each group of the plurality of voxels. As such, since the integral value is calculated for each voxel or each group of a plurality of voxels, it is possible to specify a back flow portion in more detail.

In the blood flow analysis system according to the above-described embodiment, the display control unit 14 may display an index indicating a blood flow other than the map image on the display unit 3. Specifically, as the index indicating the blood flow, an arrow indicating the flow velocity vector may be displayed so as to be superimposed on the map image or, for example, a flow line or a path line indicating a blood flow may be displayed so as to be superimposed on the map image.

In the blood flow analysis system according to the above-described embodiment, the three-dimensional medical image 6 is used to specify a back flow portion. However, the three-dimensional image is not necessarily used. For example, a two-dimensional cross-sectional image may be used to acquire a flow velocity vector by the same method as that in the above-described embodiment and a back flow portion may be specified on the basis of an integral value of the component of in the direction of the central axis of the blood vessel region.

What is claimed is:

1. A blood flow analysis apparatus comprising:
a processor configured to:
extract a blood vessel region from a blood vessel image obtained by capturing an image of an object including a blood vessel;
acquire a flow velocity vector indicating a blood flow velocity and a blood flow direction in the blood vessel region;
set a central axis which extends in an extension direction of the blood vessel region, integrate a component of the flow velocity vector in a direction of the central axis with respect to a time axis to calculate an integral value, and specify whether there is a blood back flow in the blood vessel region on the basis of a change in the integral value;
specify that there is the back flow in a case in which the integral value increases non-monotonically or in a case in which the integral value decreases non-monotonically; and
specify that there is no back flow in a case in which the integral value increases monotonically or in a case in which the integral value decreases monotonically.

2. The blood flow analysis apparatus according to claim 1, wherein the processor is configured to display a map image obtained by mapping a portion in which the back flow occurs to a coordinate axis of the blood vessel region on a display unit.

3. The blood flow analysis apparatus according to claim 2, wherein the processor is configured to generate the map image using the integral value obtained by integrating the flow velocity vector for a predetermined period.

4. The blood flow analysis apparatus according to claim 3, wherein the predetermined period is a period of one heartbeat.

5. The blood flow analysis apparatus according to claim 2, wherein the processor is configured to generate the map image in time series whenever the flow velocity vector is integrated in the direction of the time axis and display the map image as a moving image on the display unit.

6. The blood flow analysis apparatus according to claim 2, wherein the processor is configured to display the map image so as to be superimposed on a two-dimensional or three-dimensional blood vessel image.

7. The blood flow analysis apparatus according to claim 2, wherein the processor is configured to display information of an amount of the back flow on the display unit on the basis of the integral value.

8. The blood flow analysis apparatus according to claim 2, the processor is configured to display an index indicating a blood flow other than the map image on the display unit.

9. The blood flow analysis apparatus according to claim 8, wherein the index indicating the blood flow is the flow velocity vector, a flow line, or a path line.

10. The blood flow analysis apparatus according to claim 1, wherein the processor is configured to calculate the integral value for each voxel or each group of a plurality of voxels in the blood vessel region.

11. The blood flow analysis apparatus according to claim 1, wherein the processor is configured to calculate the integral value for each cross section that is orthogonal to a direction of the central axis of the blood vessel region.

12. The blood flow analysis apparatus according to claim 1, wherein the processor is configured to acquire the flow velocity vector on the basis of a three-dimensional blood vessel image captured in time series or a three-dimensional blood vessel image captured at any point of time.

13. The blood flow analysis apparatus according to claim 1, wherein the processor is configured to acquire the flow velocity vector, using a computational fluid dynamics model for the blood vessel region, a three-dimensional cine phase contrast magnetic resonance method, or a three-dimensional ultrasound image.

14. A blood flow analysis method comprising:
extracting a blood vessel region from a blood vessel image obtained by capturing an image of an object including a blood vessel;
acquiring a flow velocity vector indicating a blood flow velocity and a blood flow direction in the blood vessel region;
setting a central axis which extends in an extension direction of the blood vessel region, integrating a component of the flow velocity vector in a direction of the central axis with respect to a time axis to calculate an integral value, and specifying whether there is a blood back flow in the blood vessel region on the basis of a change in the integral value;
specifying that there is the back flow in a case in which the integral value increases non-monotonically or in a case in which the integral value decreases non-monotonically; and
specifying that there is no back flow in a case in which the integral value increases monotonically or in a case in which the integral value decreases monotonically.

15. A non-transitory computer-readable storage medium storing therein a blood flow analysis program of a blood flow analysis device that, when run, causes a processor to:
extract a blood vessel region from a blood vessel image obtained by capturing an image of an object including a blood vessel;
acquire a flow velocity vector indicating a blood flow velocity and a blood flow direction in the blood vessel region;
set a central axis which extends in an extension direction of the blood vessel region, integrate a component of the flow velocity vector in a direction of the central axis with respect to a time axis to calculate an integral value, and specify whether there is a blood back flow in the blood vessel region on the basis of a change in the integral value;

specify that there is the back flow in a case in which the integral value increases non-monotonically or in a case in which the integral value decreases non-monotonically; and specify that there is no back flow in a case in which the integral value increases monotonically or in a case in which the integral value decreases monotonically.

* * * * *